United States Patent [19]
Pierrat

[11] Patent Number: 6,023,328
[45] Date of Patent: Feb. 8, 2000

[54] PHOTOMASK INSPECTION METHOD AND APPARATUS

[75] Inventor: Christophe Pierrat, Boise, Id.

[73] Assignee: Micron Technology, Inc., Boise, Id.

[21] Appl. No.: 09/027,977

[22] Filed: Feb. 23, 1998

[51] Int. Cl.$^7$ ................................................. G01N 21/88
[52] U.S. Cl. ..................................... 356/237.4; 356/237.5
[58] Field of Search .............................. 356/237.4, 237.5

[56] References Cited

U.S. PATENT DOCUMENTS

| | | | |
|---|---|---|---|
| 5,162,867 | 11/1992 | Kohno | 356/237.5 |
| 5,337,097 | 8/1994 | Suzuki et al. | 353/101 |
| 5,701,174 | 12/1997 | Yeh et al. | 356/237.4 |
| 5,710,624 | 1/1998 | Utamura | 356/237.5 |

*Primary Examiner*—Robert H. Kim
*Assistant Examiner*—Zandra V. Smith
*Attorney, Agent, or Firm*—Schwegman, Lundberg, Woessner & Kluth P.A.

[57] ABSTRACT

A method and apparatus for inspection of masks is disclosed herein. The method comprises exposing a wafer at a large magnification, while maintaining the same intensity profile obtain at standard exposure magnifications. The enlarged image exposed on a wafer is then examined for defects. The apparatus for inspecting masks includes an illumination system, an optical imaging system, and a detecting device. During inspection of the wafer, the enlarged image on the wafer is examined for defects. In evaluating potential defects, an exposed die is compared with another exposed die to determine the location of the defect on the mask. Alternatively, the examination of the image can occur with respect to a pattern of the image on a design database.

20 Claims, 2 Drawing Sheets

PHOTOMASK INSPECTION METHOD AND APPARATUS

FIELD OF THE INVENTION

The present invention relates generally to photolithography. More particularly, it pertains to a method and apparatus for inspecting a photomask for use in photolithography.

BACKGROUND OF THE INVENTION

Photolithography involves the application of energy to photo resist deposited on a wafer. The application of energy is controlled through the use of a patterned photomask, using a step and repeat procedure where the pattern is repeated over a number of different fields. To eliminate the printability of certain defects, the pattern is reduced on the wafer using a 1/10 or a 1/5 reduction stepper. Although effective in eliminating some defects, this procedure does not eliminate all defects printed on to the wafer. Furthermore, the pattern from the photomask is repeated several times, and upon several different wafers, thus the defects of the photomask are capable of being repeated several times. Accordingly, it is important to detect and correct as many defects as possible in photomasks prior to production of the wafers.

Currently, inspecting photomasks include a number of different approaches. One approach is to inspect a photomask directly using an optical microscope. Previously, this type of inspection was done manually. However, the use of the optical microscope has evolved to automated inspection employing high resolution CCD imaging systems as the masks have become more complex. For automated photomask inspection, a die-to-database inspection is often used. The die on the photomask is compared with a design on the database used to create the photomask. In this type of inspection, a mask is illuminated from one side. An image of the mask is projected on to an image sensor, which digitizes the image. The digitized image is then directed to defect detection circuitry. The defect detection circuitry also obtains a digitized image according to the original pattern stored in the design database. The digitized pattern image also attempts to predict or model the image resulting from the exposure process. The two images are then compared for discrepancies, and the masks having discrepancies are flagged as a potential defected mask. One problem with this approach is that these programs cannot account for all of the possible variations which occur during the exposure process.

Another type of direct mask inspection technique includes a die-to-die inspection, which uses a process similar to that used in die-to-database analysis. For die-to-die analysis, two images on the mask are compared against one another. Assuming the defects are not located at the same location, the defect will be found by comparing the images of the two dies. However, both the die-to-die and the die-to-database inspection techniques have difficulty in accurately detecting defects in photomasks. As feature size continues to decrease on the photomask, conventional microscopes experience difficulty in detecting the small features, and the impact of pattern defects and optical effects increases proportionately.

Another problem with both of these techniques is that imaging of the mask conducted during inspection is very different from the imaging which is actually exposed on the wafer. During exposure of the photomask, the optical setup is quite different than that of the inspection tool. The wavelengths utilized in the exposure process and the inspection processes are different, and thus the coherence of the light is different for the two processes. The different wavelengths used in exposure and inspection can result in defects becoming difficult to detect during inspection, or creating false defects. The numerical apertures used for exposure and for inspection are also different. Therefore, defects which are detected during the inspection above process may not actually print on the wafer, and do not need to be repaired. Alternatively, some defects will not be detected and yet continue to print on the wafer.

These conventional inspection systems detect defects in the patterns themselves by inspecting the original data from which the mask is constructed, or by inspecting the mask after it is printed on the glass substrate. However, many defects are not noticeable until the feature is fleshed out in three dimensions by forming the pattern in the resist. Defects in either the mask or the resist pattern during processing can have a significant effect on the accuracy and electronic characteristics of the semiconductor device. Existing inspection methods are limited because they are unable to anticipate the defects which appear when the resist is formed on the patterned wafer. Such defects result from defects in the pattern as well as from characteristic behavior of the resist material during etching. Existing methods do not take into account the characteristics of the resist material which will be formed according to the mask pattern. As a result, a mask may be inaccurately flagged as defective when the alleged defect would not impact the final resist pattern. Alternatively, there may be a feature in the original pattern which is accurately captured in the mask pattern, but which cannot be accurately formed in the resist due to characteristics of the resist material. The mask is, as a result, inaccurately flagged defect-free when in fact, one or more defects will appear when the resist is formed according to the pattern.

Another approach to inspect a photomask is to inspect a wafer that has been shot using the photomask. A wafer is exposed using the particular photomask to be inspected, as in standard production of wafers, and then the dies on the wafer are inspected. To maintain consistency of the optical parameters during exposure and the inspection process, the wafer is exposed using the same stepper used in standard production. The wafer is then viewed under high magnification to locate defects on the wafer. After the location of these defects is determined, the defects are traced back to the photomask. For repeating defects, this approach can be quite effective. However, as feature size continues to decrease, current inspection tools are limited to certain resolutions. Therefore, some features and defects, are difficult, or sometimes impossible to view using current wafer inspection tools.

Accordingly, what is needed is a better, more reliable approach to inspect wafer defects. What is further needed is a way to inspect wafers incorporating smaller feature sizes using current inspection machines.

SUMMARY OF THE INVENTION

The present invention is directed to a method for inspecting a mask used in an exposure step of a process of manufacturing a semiconductor device. A test substrate is exposed using a photomask which is to be inspected. The photomask is exposed on to the test substrate forming an image thereon which is larger than images formed during conventional exposure methods.

The method includes the steps of providing a test substrate, aligning a mask with the test substrate, and exposing the test substrate at a magnification higher than that used during standard production. The provided mask can have a pattern which contains either a single field or a plurality of fields thereon. Radiation is projected on the mask, where projecting the radiation forms an image of the field or fields on the test substrate. The formed images are larger than one of the fields on the mask.

In another embodiment, the images are formed larger than those used during standard production, while the optical parameters are maintained consistent with those used during standard production of wafers. This creates an aerial image on the test wafer which is similar to that created during standard production of wafers. The optical parameters for maintaining a consistent aerial image include the numerical aperture, spacial coherency, and wavelength. The effects of the resist are the same on the test wafer as those during standard production, thereby creating a realistic sample wafer to inspect, while facilitating the use of conventional inspection equipment.

An inspection system is also provided which includes an illumination source, a condenser lens, and a projection lens all operatively coupled with an optical control. A test substrate retention member holds a test substrate therein. A mask is provided between the test substrate and the illumination source such that radiation from the illumination source passes through the mask to form an enlarged image on the test substrate. The test substrate, in one embodiment, comprises a wafer.

The provided method of mask inspection and inspection apparatus uses a new combination in an unanticipated manner. The magnified image exposed on the test substrate experiences the same optical parameters as a wafer during a conventional exposure process. The image accurately models defects and can be inspected using conventional inspection tools. Defects which are otherwise undetected are detected using the process. Furthermore, the number of false defects is reduced.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope of the present invention is defined by the appended claims.

Figure 1:
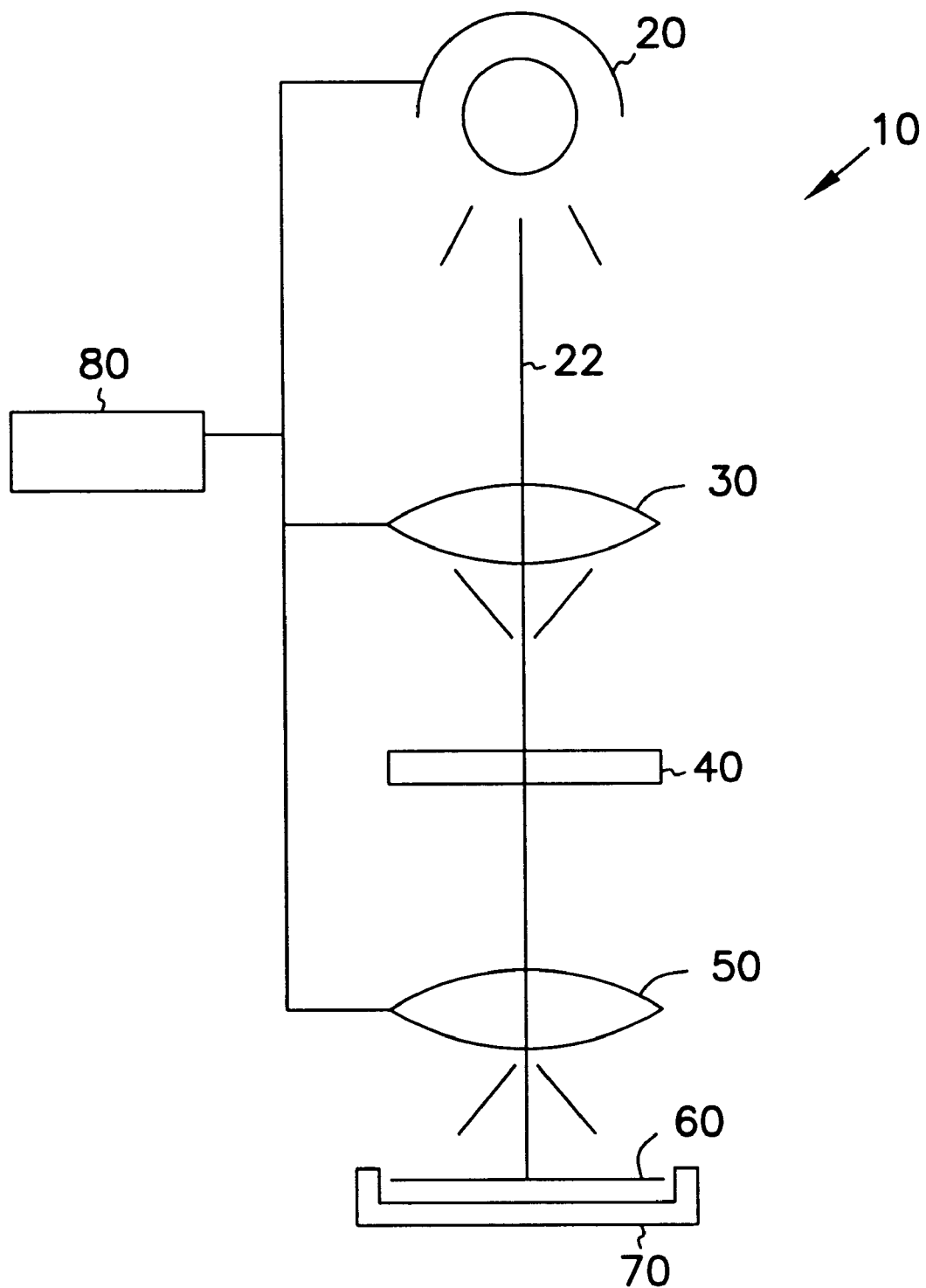
FIG. 1 is a block diagram illustrating an inspection system constructed in accordance with one embodiment of the present invention.

FIG. 1 illustrates a block diagram showing a system 10 with a first embodiment of the present invention. The inspection system 10, which uses Köhler illumination, includes an illumination source 20, a condenser lens 30, a mask 40, a projection lens 50, a test substrate 60, and a stage and wafer hold 70. The mask 40 has a pattern disposed thereon which forms an image when radiation is projected on the mask 40.

The illumination source 20 is disposed proximate to the condenser lens 30. The mask 40 is disposed between the illumination source 20 and projection lens 50 such that radiation from the illumination source projects an image from the mask 40 on the test substrate 60, as will be described further below.

The illumination source 20 provides a beam of light 22 to the condenser lens 30. The condenser lens 30 converges the light 22 to a pupil entrance of the projection lens 50. The pattern of the mask 40 is projected using the projection lens 50. The projection lens 50 magnifies and projects the pattern on the test substrate 60, thereby forming an image on the test substrate 60. The test substrate 60 has a coating of photoresist or other energy sensitive coatings, which can be developed after the wafer is exposed. In one embodiment, the test substrate 60 comprises a wafer.

The inspection system 10 also has an optical control 80. The optical control 80 operates similar to those in aerial image measurement systems manufactured by Carl Zeiss, Inc., which are known to those skilled in the art. The aerial image measurement systems are systems which capture digital images of masks and which are exposed under conditions that are essentially equivalent to a conventional stepper. As the exposure light of the aerial image measurement system radiates through the mask, an ultra-violet sensitive CCD camera is used for data capture of the mask image.

For the inspection system 10, the optical control mechanism 80 is operatively coupled with the illumination source 20, the condenser lens 30, and the projection lens 50 and manipulates several optical parameters of the inspection system 10. The optical parameters which can be controlled by the optical control 80 include the wavelength of the light source, the filling factor, and the numerical aperture of the projection lens. Using these optical parameters, the spatial coherence of the light can also be manipulated. The optical control 80 of the present invention allows for manipulation of the spatial coherency of the light by altering the numerical aperture and the size of the illumination source 20.

In addition to changing the optical parameters discussed above, the optical control 80 also can manipulate the magnification of the image formed on the test substrate 60. During standard production of wafers using steppers, the image exposed on the wafer is reduced to very small feature sizes. For instance, some steppers reduce the fields on the mask to $\frac{1}{10}$ of the original size when exposed on the wafer. However, the inspection system 10 is used to magnify the image formed on the test substrate 60. Using the optical parameters discussed above, the optical control 80 adjusts optical parameters to maintain an intensity profile that is equivalent to that produced during conventional stepper photolithography processes while creating a magnified image on the test substrate. The optical parameters can be modified before or during to achieve the appropriate intensity profile. The image created on the test substrate is much larger than in the conventional process, yet the profile or aerial image remains the same, and the intensity profile is accurately recorded on the test substrate. In the conventional exposure process, the stepper process produces a very small feature size, and therefore the intensity profile cannot be accurately recorded.

Figure 2:
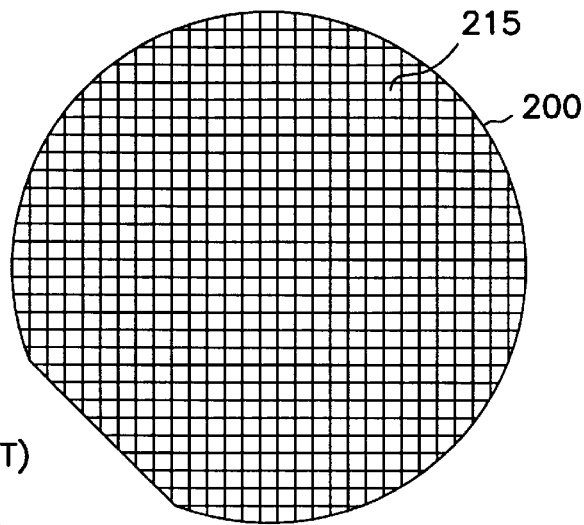
FIG. 2 is a first side view illustrating a production wafer used in standard exposure processes.

During typical exposure processes for the production of wafers, a stepper is used to expose a mask at a ⅒ or ⅕ reduction. FIG. 2 illustrates an example of a wafer 200 exposed using a stepper during standard production of a photomask. The design details are minute, and these details are further reduced during production. During standard production, a plurality of fields 215 are reduced while being exposed, which are later inspected using high magnification optical microscopes or automated inspection machines. Either approach requires high magnification of the wafer during the inspection process since the feature size on the wafer 200 was designed with very small features, and has been further reduced during fabrication. Even implementing high magnification in conventional inspection systems, defects printed on the wafer are difficult to detect due to the limited capabilities of conventional inspection devices and the tiny feature sizes of the photomasks.

Figure 3:
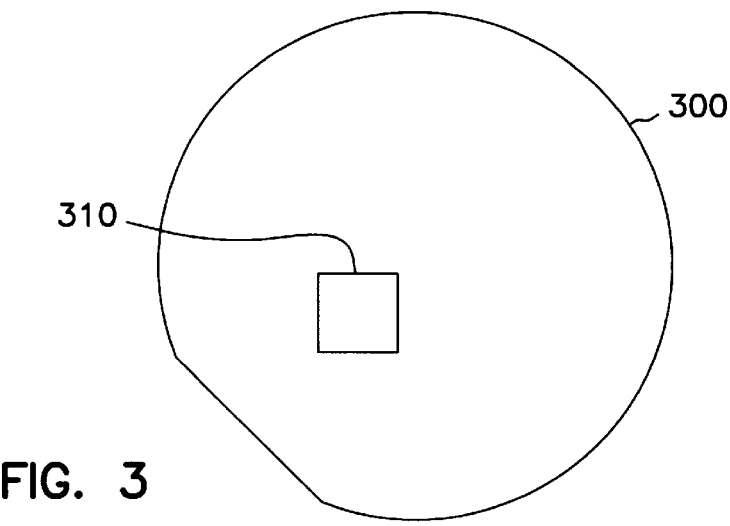
FIG. 3 is a first side view illustrating a test wafer constructed in accordance with one embodiment of the present invention.
Figure 4:
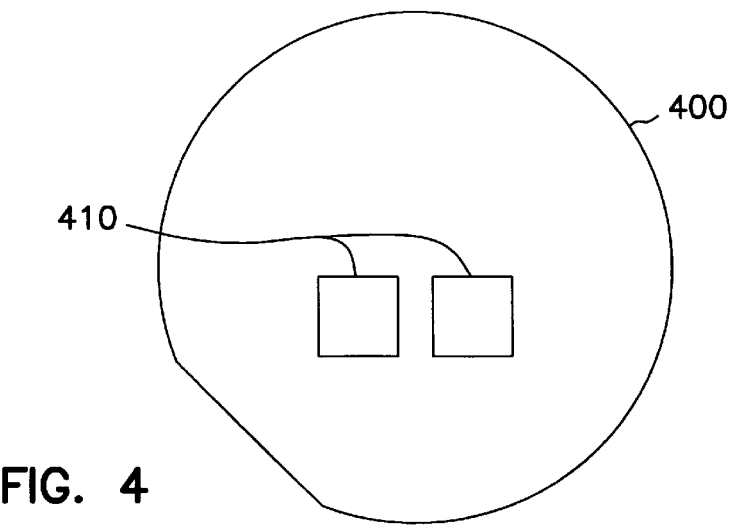
FIG. 4 is a first side view illustrating a test wafer constructed in accordance with another embodiment of the present invention.

A test wafer 300 made in accordance with the present invention is shown in FIG. 3. One field of the photomask is exposed at a higher magnification than is produced using the stepper process discussed above. An enlarged image 310 is formed thereon using the inspection system 10. In another embodiment, as illustrated in FIG. 4, at least two enlarged images 410 are formed on a test wafer 400 using the inspection system 10. The test wafer 300 can be viewed and also inspected using conventional methods such as an optical microscope, or commercially available wafer inspection tools. The small feature sizes have been magnified during exposure and are therefore easier to view during the inspection process. In another embodiment, an energy sensitive device is used to capture the enlargened image 310. Alternatively, other structures having energy sensitive coatings can also be formed and are considered within the scope of the invention. It should be further noted that the shape of the test substrate 300 can take on a number of different shapes.

During use of the present invention, a test substrate is used to perform the inspection and the photomask is magnified during exposure on to the test substrate. For one example, an eight inch wafer is provided, and normally ninety fields are printed on to the wafer. The stepper in conventional production of wafers would be stepping 90 times across the wafer. Within this field, there may be four to twenty dies. Using the stepper in this conventional process, the image is formed on the wafer typically using a 5 to 1 or a 4 to 1 reduction of the image.

Using the inspection system 10, in one embodiment, an image is formed on the test substrate which is magnified by at least a factor of 2, instead of reducing it by a factor of 4, or other conventional reduction values. Thus, a die is printed that would be eight times bigger than a die printed by conventional stepper methods. However, the optical control 80 maintains substantially the same the intensity profile on the test substrate as those on a wafer during standard production of the wafer. Alternatively, other magnification factors could be implemented, and are considered within the scope of the invention. The above example is provided for illustrative purposes only. Those skilled in the art will readily recognize that these numbers are exemplary only, and that the amount of magnification of the image may vary, and not exceed the scope of the present invention.

After the test substrate 60 has been exposed using the inspection apparatus 10, the test substrate 60 can be further examined for defects by a number of processes. For instance, the test substrate 60 can be manually viewed under high magnification to visually inspect for defects. The enlarged image on the test substrate 60 facilities manual inspection of the test substrate 60 using conventional microscopes since the image has been magnified. Alternatively, the test substrate 60 can be compared with a simulated image of the mask pattern for the test substrate 60. In yet another embodiment, the test substrate 60 can be compared with another test substrate 60 or another enlarged image of the same test substrate 60 which has also been exposed with the same pattern, and any discrepancies between the test substrates would reveal potential defects on the test substrate 60. After finding the location of a defect on the test substrate 60, the defect on the mask can be located. The image on the test substrate 60 is located and its position on the substrate 60 is determined. Then, the positioned is cross-referenced to the relative position on the mask using the design layout of the mask. After locating the defect on the mask, the mask can then be corrected using a variety of techniques as known by those skilled in the art.

Advantageously, the provided method of inspection and inspection apparatus uses a new combination of conventional components in an unanticipated manner. The image formed on the wafer is magnified before it is exposed on the wafer, and before it is inspected. The magnified image exposed on the wafer allows small defects to be detected during the inspection process. Since the image is magnified, conventional inspection equipment can be used to view the exposure, even as the details of the image continue to decrease in size. A further benefit of the claimed method and apparatus is that the aerial image of the test wafer is maintained consistent with the aerial image of a wafer exposed using the stepper process. Defects which would otherwise be undetected are detected using this new method and apparatus. Several different types of defects can be detected with the present invention that are not normally detectable by present inspection systems, or are difficult to detect. The number of inaccurate classification of false defects is reduced. Additionally, resist effects can also be accurately modeled and observed, thereby creating a test substrate having an identical aerial profile as a wafer exposed using the conventional stepper exposure process.

It is to be understood that the above description is intended to be illustrative, and not restrictive. Many other embodiments will be apparent to those of skill in the art upon reviewing the above description. For instance, other devices, such as a magnified stepper, could be used to magnify the image formed on the test wafer. Alternatively, another test product having a energy sensitive qualities similar to that disposed on the wafer could be used for forming the enlargened image thereon. The scope of the invention should, therefore, be determined with reference to the appended claims, along with the full scope of equivalents to which such claims are entitled.

What is claimed is:

1. A method for uncovering defects on a photomask, the method comprising the acts of:

aligning a mask with a test substrate having energy sensitive coating thereon, said mask having a pattern of at least one field thereon; and projecting radiation on the mask thereby forming an image of the field on the test substrate, said image on the test substrate formed larger than said field on said mask.

2. The method of claim 1, wherein the step of projecting radiation on the mask comprises the step of magnifying the image by at least a factor of two.

3. A method for uncovering defects on a photomask, the method comprising the acts of:

aligning a mask with a wafer, said mask having a pattern of at least one field thereon; and projecting radiation on the mask thereby forming an image of the field on the wafer, said image being larger than said field on said mask.

4. The method of uncovering defects as recited in claim 3, wherein the act of projecting radiation on the mask includes forming said image on the wafer larger than a plurality of fields.

5. The method of uncovering defects as recited in claim 3, wherein the step of aligning the mask with the wafer includes the step of retaining the wafer in a stage and wafer hold.

6. The method of claim 3, wherein the wafer is first coated with a resist prior to exposure to the radiation.

7. The method of claim 5, wherein the resist is processed following each exposure to radiation.

8. A method for uncovering defects on a photomask, the method comprising the acts of:

providing a wafer;

aligning a photomask with the wafer, said photomask having a pattern thereon;

projecting radiation on the photomask thereby forming an image on the wafer, said image being larger than said field on said mask; and viewing the wafer.

9. The method as recited in claim 8, wherein the act of projecting radiation on the photomask comprises forming a plurality of images on the wafer.

10. The method as recited in claim 9, wherein the act of viewing the wafer includes the act of inspecting the wafer, wherein one of the plurality of images is compared with at least one other formed image on the wafer.

11. The method as recited in claim 8, wherein the act of viewing the wafer includes the act of inspecting the wafer, wherein at least one of the plurality of formed images is compared with a design image of a database.

12. The method as recited in claim 8, wherein the act of viewing includes the act of inspecting the wafer comprising the acts of:

determining a location of a defect on the wafer for establishing a position of said defect; and determining a location of a mask defect using said position of said defect on the wafer.

13. A method for uncovering defects on a photomask, the method comprising the acts of:

providing a test wafer;

aligning a photomask with the test wafer, said photomask having a pattern thereon; and projecting radiation from an exposure device on the photomask thereby forming a magnified image on the wafer, said image being larger than said field on said mask; and maintaining an intensity profile substantially similar to that of a conventionally produced wafer using an optical control.

14. The method as recited in claim 13, wherein the step of maintaining the intensity profile includes modifying the optical parameters before the step of projecting the radiation from the exposure device.

15. The method as recited in claim 13, wherein the step of maintaining the intensity profile includes modifying the optical parameters during the step of projecting radiation from the exposure device.

16. The method as recited in claim 13, wherein the act of modifying the optical parameters includes modifying a numerical aperture.

17. A system for inspecting a mask, the system comprising:

a retention member;

a test substrate having an energy sensitive coating thereon, the test substrate being held by the retention member;

an illumination source;

a first lens having a modifiable aperture, the first lens disposed proximate to the illumination source;

a second lens disposed between the first lens and the test substrate;

an optical control operatively coupled with the first lens, the second lens, the aperture, and the illumination source; and a mask having a pattern thereon, the mask being disposed between the first lens and the second lens;

where radiation from the illumination source passes through the mask to form an enlarged image on the test substrate.

18. The system for inspecting a mask as recited in claim 17, wherein the first lens is a condenser lens, and the second lens is a projection lens.

19. The system for inspecting a mask as recited in claim 17, wherein the retention member comprises a stage and wafer hold.

20. The system for inspecting a mask as recited in claim 17, wherein the test substrate comprises a wafer.

* * * * *